(12) United States Patent  (10) Patent No.: US 7,857,169 B2
Harrold  (45) Date of Patent: Dec. 28, 2010

(54) RECTANGULAR METERED DISPENSER WITH FEED-CONTAINING PISTON DRIVE MECHANISM

(75) Inventor: John E. Harrold, Bloomsbury, NJ (US)

(73) Assignee: Innopak, Inc., Brick, NJ (US)

( * ) Notice: Subject to any disclaimer, the term of this patent is extended or adjusted under 35 U.S.C. 154(b) by 17 days.

(21) Appl. No.: 12/460,568

(22) Filed: Jul. 21, 2009

(65) Prior Publication Data

US 2009/0287169 A1 Nov. 19, 2009

Related U.S. Application Data

(62) Division of application No. 11/315,694, filed on Dec. 22, 2005, now Pat. No. 7,726,520.

(51) Int. Cl.
B67D 7/84 (2010.01)
(52) U.S. Cl. .................. 222/162; 222/256; 222/340; 222/386
(58) Field of Classification Search ................ 222/162, 222/383.1, 386, 256, 340, 341, 380, 402.2
See application file for complete search history.

(56) References Cited

U.S. PATENT DOCUMENTS

| 3,754,687 | A | 8/1973 | Norton |
|---|---|---|---|
| 3,934,585 | A | 1/1976 | Maurice |
| 4,091,677 | A | 5/1978 | Oshikubo |
| 5,226,895 | A | 7/1993 | Harris |
| 5,267,986 | A | 12/1993 | Py |
| 5,401,259 | A | 3/1995 | Py |
| 5,613,957 | A | 3/1997 | Py |
| 5,685,869 | A | 11/1997 | Py |
| 6,413,246 | B1 | 7/2002 | Harrold |
| 6,419,663 | B2 | 7/2002 | Harrold |

*Primary Examiner*—Kevin Shaver
*Assistant Examiner*—Stephanie E Williams
(74) *Attorney, Agent, or Firm*—Kenneth P. Glynn, Esq.; Deirdra M. Meagher, Esq.

(57) ABSTRACT

A metered dispenser includes a housing including a reciprocal piston drive stem including an inlet opening at a first end thereof, a floating piston at a second end, and a passage between the first and second ends. An inlet valve is provided adjacent the first end for permitting entry of liquid product into the passage. A biased cocking mechanism is reciprocally disposed substantially within the housing. A biased loading mechanism is movable in a second generally opposite direction by the cocking mechanism, and is engageable with the piston drive stem to move the drive stem in the second direction. When the cocking mechanism is moved from an initial rest position toward the second direction, a series of operations allow the loading mechanism to project the drive stem in the first direction to dispense a metered dose of liquid product through a discharge orifice provided adjacent the second end.

17 Claims, 9 Drawing Sheets

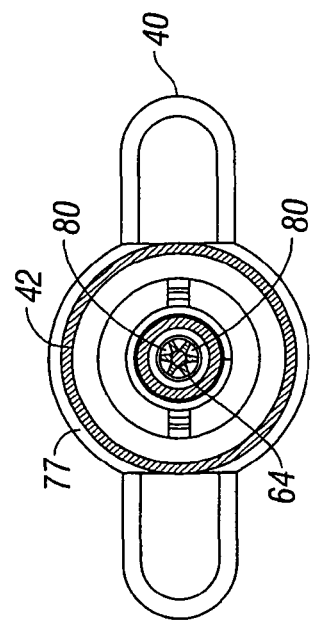
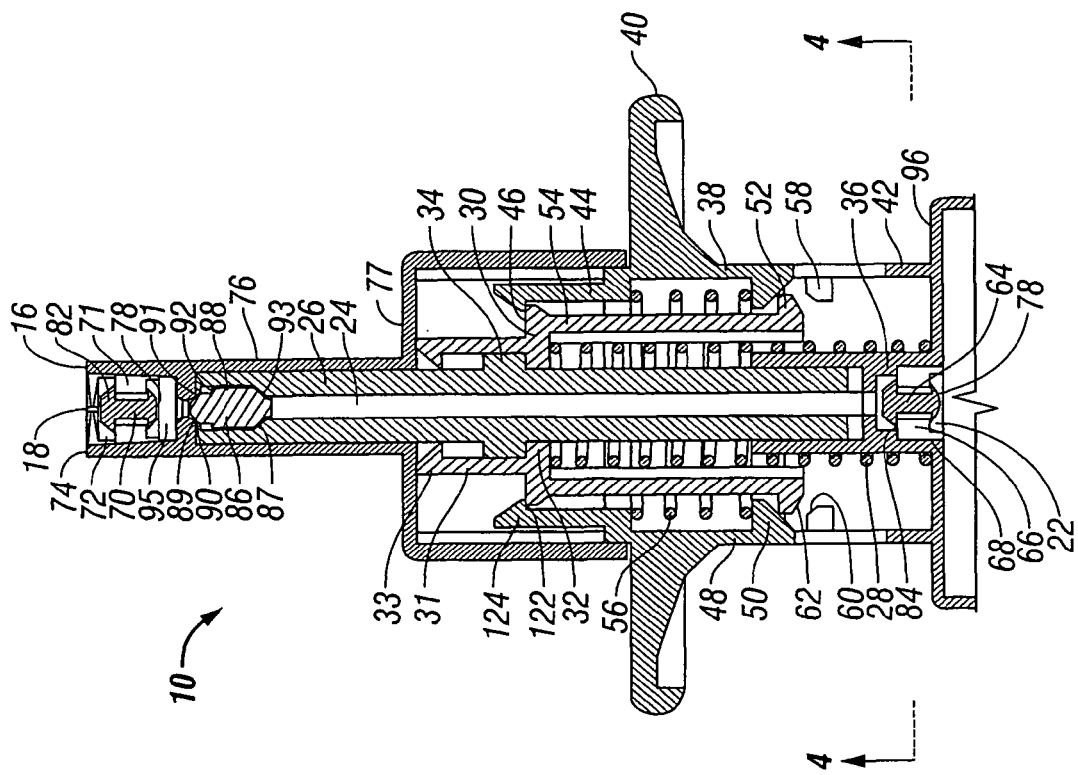
FIG. 4
FIG. 3

RECTANGULAR METERED DISPENSER WITH FEED-CONTAINING PISTON DRIVE MECHANISM

REFERENCE TO RELATED APPLICATIONS

This patent application is a divisional application of U.S. patent application Ser. No. 11/315,694, filed on Dec. 22, 2005, now U.S. Pat. No. 7,726,520, and entitled "Metered Dispenser With Feed-Containing Piston Drive Mechanism" by the same inventor herein.

BACKGROUND OF INVENTION a. Field of Invention

The invention relates generally to liquid dispensers, and, more particularly, to a mechanically propelled metered dispenser for dispensing a predetermined quantity of liquid product.

b. Description of Related Art

Finger-powered dispensing pumps are known in the art, and generally include a finger operated pump head, which when depressed, discharges liquid product from a container having the pump mounted thereon. An exemplary finger-powered dispensing pump is disclosed in U.S. Pat. No. 3,414,169. Such pumps can be arranged as sprayers or atomizers in which a spray nozzle emits the pumped liquid as a spray, as shown in U.S. Pat. Nos. 3,194,447 and 4,433,799. Alternatively, the pumps can be arranged as liquid dispensers in which a dispensing nozzle thereof is a discharge spout, as shown in U.S. Pat. No. 3,216,625.

It is desirable that means be provided for metering the amount of liquid dispensed, and also that such means be easy for a consumer to operate. For example, if the pump is used on a spray dispensing bottle for a hair spray, a consumer may desire a generally repeatable amount of spray dispensed per pump actuation. However, if the pump is used with a medicine dispensing bottle, it is desirable that the dispensed amount be repeatable and precise for imparting the intended effect.

Such an exemplary metered dispenser for dispensing of medicine is disclosed in U.S. Pat. No. 5,613,957 to Py. Specifically, referring to FIG. 1 of Py, there is disclosed an apparatus (10) for applying medicament and generally including an outer body (12), an inner body (14) and a piston body (16). When piston body (16) is located in the up position (see FIG. 1), medicament is permitted to flow from medicament chamber (33), through slots (46), and drop cavity (38) to fill the drop cavity. When piston body (16) is pushed toward outer body (12) and into a down position, the downward stroke of piston (18) forces the medicament in drop cavity (38) through channel (44) and into interface (25). During this downward stroke of piston (18), flexible rim (40) is forced outwardly into contact with cylindrical wall (36), thus preventing the passage of medicament in drop cavity (38) back into medicament chamber (33). The pressurized medicament flowing through channel (44) opens interface (25) by forcing flexible outer nozzle portion (22) away from inner nozzle portion (24) to open the nozzle and release the medicament. Once the medicament is released, outer nozzle portion (22) returns to its normal position in contact with inner nozzle portion (24) so as to close interface (25).

As readily evident from the afore-described operation of the Py metered dispenser, the dispenser requires piston body (16) to be pushed toward outer body (12) for dispensing of medicine through nozzle (20). When used adjacent an eye or a nostril for dispensing medicine, such a pushing action can lead to contact of the nozzle tip with a user's eye to contaminate the dispenser, and more importantly, can present a danger to the user's eye during repeated use if the nozzle tip indeed becomes contaminated. Yet further, since the amount of medicine dispensed is a function of piston body (16) which is pushed toward outer body (12), the amount of medicine dispensed can vary depending on whether a user completely pushes piston body (16) toward outer body (12), which can also be a function of a user's ability to push piston body (16) as required.

It would therefore be of benefit to provide a metered dispenser which is repeatable in operation to dispense a predetermined dosage of medicine or other products, and which is usable by a broad range of users to repeatedly dispense a metered dosage of medicine without fluctuations in the amount of medicine dispensed. It would also be of benefit to provide a metered dispenser which is simple and economical to manufacture and assemble, and which is robust in design and efficient to operate.

The following patents are representative of metered dispensers with feed-containing piston drive mechanisms:

U.S. Pat. No. 3,754,687 to Robert W. Norton describes a pipetting dispenser of the piston-cylinder type with interchangeable fittings by which the operative movement of the piston may be arranged to be in line with or at an angle to the axis of an attached pipette and having adjustable stop means to limit travel of the piston within predetermined limits, together with means automatically retracting the piston from its discharge position to a position in engagement with said adjustable stop means, thereby insuring the repeated dispensing of the like volumes of liquid from said pipette in successive operations of the dispenser, for any adjusted position of the stop means.

U.S. Pat. No. 3,934,585 to David M. Maurice discloses a method and apparatus for applying therapeutic eye drops to the eye by metering a predetermined volume of fluid and rapidly applying a pressure to one end of the metered fluid for forcing the fluid from a nozzle of means defining a small passageway such as and open-ended tube as a droplet having sufficient velocity to travel a generally horizontal distance in space to the eye. Unit dose application and multiple dose applications are included and provision is made for preventing anticipatory blinking of the eye during self-administration.

U.S. Pat. No. 4,091,677 to Yuji Oshikubo describes a pipetting apparatus comprising a housing, a liquid receiving tube attached to the lower end of the housing and receiving a predetermined amount of a liquid sample herein, a cylinder piston device disposed in the housing for applying vacuum pressure on the upper end of the liquid receiving tube for sucking a liquid sample into the tube, a manually operable device for actuating the cylinder piston device, an air inlet for directing compressed air into the housing, and a manually operable valve for directing compressed air either to the upper end of the liquid receiving tube or to atmosphere.

U.S. Pat. No. 5,226,895 to Dale C. Harris describes a present invention which relates to a hypodermic syringe having the same general appearance as a pen which is specifically adapted to provide for multiple measured injections of materials such as insulin or human growth hormone.

U.S. Pat. No. 5,267,986 to Daniel Py describes and illustrates a cartridge for actuating a piston-like or accordion-like dispenser-vial for applying medication to any eye. The cartridge includes a housing for holding the dispenser-vial and a telescoping cylinder for compressing the dispenser-vial in the longitudinal direction to actuate the vial. The cartridge includes a locking mechanism for locking the telescoping cylinder to restrict its movement and a trigger mechanism for releasing the cylinder from the locked position so that a drop is released form the dispenser. The housing includes a finger for engaging the lower eyelid and exposing the conjunctival cul de sac.

U.S. Pat. No. 5,401,259 to Daniel Py discloses a cartridge for actuating a piston-like or accordion-like dispenser-vial for a applying medicament to an eye. The cartridge includes a housing for holding the dispenser-vial and a telescoping cylinder for compressing the dispenser-vial in the longitudinal direction to activate the vial. The cartridge includes a locking mechanism for locking the telescoping cylinder to restrict its movement and a lever mechanism for releasing the cylinder from the locked position so that a drop is released from the dispenser. The housing includes a finger for engaging the lower eyelid and exposing the conjunctival cul-de-sac.

U.S. Pat. No. 5,613,957 to Daniel Py discloses an apparatus used for applying medicament to an eye and to store the medicament in a medicament chamber. A nozzle is coupled in fluid communication with the medicament chamber and is formed by an outer nozzle portion and an inner nozzle portion received within the outer nozzle portion. A tight interface is defined between the inner nozzle portion and the outer nozzle portion and is normally in a closed position to prevent the passage of medicament through the nozzle. The interface opens in response to the flow of medicament of sufficient pressure into it to permit the passage of medicament through the nozzle for release into the eye.

U.S. Pat. No. 5,685,869 to Daniel Py describes and illustrates an apparatus used to apply medicament to an eye and to store the medicament in a medicament chamber. A nozzle is couples in fluid communication with the medicament chamber and is formed by an outer nozzle portion and an inner nozzle portion received within the outer nozzle portion. A seam is formed by the interface of the inner nozzle portion and the outer nozzle portion and is normally in a closed position to prevent the passage of medicament through the nozzle. The seam opens in response to the flow of medicament or sufficient pressure into the seam to permit the passage of medicament through the nozzle for release into the eye.

U.S. Pat. No. 6,413,246 B1 to John E. Harrold describes a present invention that relates to a metered, mechanically propelled, liquid dispenser. It has a main body cylinder having liquid and liquid advancing mechanism for advancing the liquid into a metered dosage dispensing chamber. There is a cocking mechanism which includes a lock pin, a stressed slot and rest slot. When the cocking mechanism is locked, the advancing means is moved and liquid is ready for firing from the metered dosage dispensing chamber through a dispensing orifice. The cocking mechanism is slowly rotated while holding the main body cylinder vertically and the pin is manually moved in the rest slot thereby causing a plunger to be forced by a spring to push against a stop on a trigger which advances the trigger to rapidly force the liquid out of the metered dosage dispensing chamber through the dispensing orifice. The dispensing orifice includes a one-way valve which allows the liquid to be dispensed while preventing air from returning to the device.

U.S. Pat. No. 6,419,663 B2 to John E. Harrold describes a present invention mechanically propelled, liquid metered dispenser includes a main housing with liquid storage and a liquid advancing component for either allowing liquid to flow out or assisting in the flow of liquid out of the main housing by exerting pressure, into a metered dosage dispensing chamber in response to a loading movement of a cocking mechanism. The chamber has an inlet connected to the main housing with a one-way valve to only permit flow of liquid into the chamber. The chamber also has an outlet orifice for dispensing liquid therefrom in a metered amount. The chamber has a reciprocal plunger and has a load and release component connected to it, which includes a cocking mechanism, a locking mechanism, and a spring. The cocking mechanism is functionally connected to the plunger so as to move in harmony therewith, or, more preferably, to move a relatively, short distance relative to the distance traveled by the cocking mechanism.

Notwithstanding the prior art, the present invention is neither taught nor rendered obvious thereby.

SUMMARY OF INVENTION

The invention solves the problems and overcomes the drawbacks and deficiencies of prior art metered dispenser designs by providing a manually operable metered dispenser including a housing having a reciprocal piston drive stem including an inlet opening at a first end thereof, a floating piston disposed at a second end thereof, and a passage between the first and second ends. An inlet valve may be provided adjacent the first end for permitting entry of liquid product into the passage, and an outlet valve may be provided adjacent the second end. A cocking mechanism may be reciprocally disposed substantially within the housing, and may be biased in a first direction. A loading mechanism may be biased in the first direction, movable in a second generally opposite direction by the cocking mechanism, and engageable with the piston drive stem to move the piston drive stem in the second direction. The loading mechanism may be further engageable with one or more stops provided in the housing.

For the metered dispenser described above, when the cocking mechanism is moved from an initial rest position toward the second direction, the cocking mechanism moves the loading mechanism and along therewith the piston drive stem in the second direction. Further, during movement of the loading mechanism in the second direction, the loading mechanism engages the stop, and during continued movement of the cocking mechanism in the second direction, the loading mechanism is disengaged from the stop to project in the first direction by the loading mechanism bias, and along therewith, project the piston drive stem in the first direction to dispense a metered dose of liquid product through a discharge orifice provided adjacent the second end.

For the metered dispenser described above, the dispenser may be connectable to a pressurized or non-pressurized storage container having the housing formed integrally with the container. Alternatively, the dispenser may be connectable to a pressurized or non-pressurized storage container, and the housing may be formed separately from the container. The cocking mechanism may include a handle for permitting manual movement of the cocking mechanism toward the second direction. The inlet and outlet valves may be one-way valves for respectively permitting flow of liquid product into the passage and out through the discharge orifice. In an exemplary embodiment, the cocking mechanism may be biased by a first coil spring disposed substantially around the loading mechanism, and the loading mechanism may be biased by a second coil spring disposed substantially around the piston drive stem. In the noted exemplary embodiment, the first coil spring may have a diameter greater than the second coil spring.

For the metered dispenser described above, the loading mechanism may include one or more substantially rigid arms including a catch element engageable with a shoulder on the piston drive stem for moving the piston drive stem in the second direction. The loading mechanism may include one or more legs including a catch element engageable with the stop to retain the loading mechanism in a loaded configuration during movement of the cocking mechanism from the initial rest position toward the second direction. The catch element of the legs may include a tapered surface engageable with a respective tapered surface on the stop to deflect the loading mechanism leg radially inwards and allow engagement of the loading mechanism catch element with the stop during movement of the cocking mechanism from the initial rest position toward the second direction.

Yet further, for the metered dispenser described above, the cocking mechanism may include one or more legs including a release tab engageable with the catch element on the loading mechanism leg to disengage the loading mechanism from the stop during continued movement of the cocking mechanism in the second direction. The release tab may include a tapered surface for moving the catch element on the loading mechanism leg radially inwards to disengage the loading mechanism from the stop. The cocking mechanism may include one or more flexible arms including a finger engageable with the loading mechanism. The flexible arm may be deflected outwards during continued movement of the cocking mechanism in the second direction to release the loading mechanism from the cocking mechanism and allow the loading mechanism to project the piston drive stem toward the first direction.

In a particular embodiment, the dispenser may be connectable to a pressurized or non-pressurized storage container including a sealed chamber defined by a container wall, an upper surface including the inlet valve and a lower surface including a spring biased piston for pressurizing liquid disposed within the chamber. The container may include a lower end having a removable container closure for retaining the spring biased piston. The container closure may include one or more release arms for retaining the spring biased piston in a first position. The release arm may further include a detent engageable by a piston plug insertable in an opening in the spring biased piston to release the spring biased piston from the first position for pressurizing liquid disposed within the chamber. When the cocking mechanism is moved from the initial rest position toward the second direction, the floating piston is allowed to move within an area at the second end to allow liquid product to enter from the passage into a metering chamber between the floating piston and the outlet valve for allowing the metered dose of liquid product to be dispensed through the discharge orifice when the piston drive stem is projected in the first direction.

In alternative embodiments of the present invention, the dispenser may be connectable to a storage container including a sealed chamber defined by a container wall, an upper surface including the inlet valve and a lower surface including a floating piston. Alternatively, the dispenser may be connectable to a pressurized storage container including a sealed chamber defined by a container wall, an upper surface including the inlet valve and a lower surface including an externally threaded piston engageable with complementary internal threads in the container for pressurizing liquid disposed within the sealed chamber upon rotation of the piston.

Further, for the metered dispenser described above, the container may include a circular or a rectangular profile. The cocking mechanism may be spring biased to return to the initial rest position. The dispenser may be usable for nasal and/or eye-care, and the metered dose may be dispensed as a spray or a fine mist.

The invention further provides a manually operable metered dispenser including a housing having a reciprocal piston drive stem including an inlet opening at a first end thereof, a floating piston disposed at a second end thereof, and a passage between the first and second ends. An inlet valve may be provided adjacent the first end for permitting entry of liquid product into the passage, and an outlet valve may be provided adjacent the second end. A cocking means may be reciprocally disposed substantially within the housing, and may be biased in a first direction. A loading means may be biased in the first direction, movable in a second generally opposite direction by the cocking means, and engageable with the piston drive stem to move the piston drive stem in the second direction. The loading means may be further engageable with one or more stops provided in the housing.

For the metered dispenser described above, when the cocking means is moved from an initial rest position toward the second direction, the cocking means moves the loading means and along therewith the piston drive stem in the second direction. Further, during movement of the loading means in the second direction, the loading means engages the stop, and during continued movement of the cocking means in the second direction, the loading means is disengaged from the stop to project in the first direction by the loading means bias, and along therewith, project the piston drive stem in the first direction to dispense a metered dose of liquid product through a discharge orifice provided adjacent the second end.

For the metered dispenser described above, in an exemplary embodiment, the dispenser may be connectable to a pressurized or non-pressurized storage means having the housing formed integrally with the storage means. Alternatively, the dispenser may be connectable to a pressurized or non-pressurized storage means, and the housing may be formed separately from the storage means. The cocking means may include a handle for permitting manual movement of the cocking means toward the second direction. The inlet and outlet valves may be one-way valves for respectively permitting flow of pressurized liquid product into the passage and out through the discharge orifice. The cocking means may be biased by a first spring (which in an exemplary embodiment may be a coil spring) disposed substantially around the loading means, and the loading means may be biased by a second (which in an exemplary embodiment may also be a coil spring) spring disposed substantially around the piston drive stem. In the noted exemplary embodiment of the present invention, the first coil spring may have a diameter greater than the second coil spring.

For the metered dispenser described above, the loading means may include one or more substantially rigid arms including a catch element engageable with a shoulder on the piston drive stem for moving the piston drive stem in the second direction. The loading means may include one or more legs including a catch element engageable with the stop to retain the loading means in a loaded configuration during movement of the cocking means from the initial rest position toward the second direction. The loading means catch element may include a tapered surface engageable with a respective tapered surface on the stop to deflect the loading means leg radially inwards and allow engagement of the loading means catch element with the stop during movement of the cocking means from the initial rest position toward the second direction.

Yet further, for the metered dispenser described above, the cocking means may include one or more legs including a release tab engageable with the catch element on the loading means leg to disengage the loading means from the stop during continued movement of the cocking means in the second direction. The release tab may include a tapered surface for moving the catch element on the loading means leg radially inwards to disengage the loading means from the stop. The cocking means may include one or more flexible arms including a finger engageable with the loading means. The flexible arm may be deflected outwards during continued movement of the cocking means in the second direction to release the loading means from the cocking means and allow the loading means to project the piston drive stem toward the first direction.

In a particular embodiment, the dispenser may be connectable to a pressurized storage means including a sealed chamber defined by a storage means wall, an upper surface including the inlet valve and a lower surface including a spring biased piston for pressurizing liquid disposed within the chamber. The storage means may include a lower end having a removable storage means closure for retaining the spring biased piston. The storage means closure may include one or more release arms for retaining the spring biased piston in a first position. The release arm may further include a detent engageable by a piston plug insertable in an opening in the spring biased piston to release the spring biased piston from the first position for pressurizing liquid disposed within the chamber. When the cocking means is moved from the initial rest position toward the second direction, the floating piston is allowed to move within an area at the second end to allow liquid product to enter from the passage into a metering chamber between the floating piston and the outlet valve for allowing the metered dose of liquid product to be dispensed through the discharge orifice when the piston drive stem is projected in the first direction.

In alternative embodiments of the present invention, the dispenser may be connectable to a storage means including a sealed chamber defined by a storage means wall, an upper surface including the inlet valve and a lower surface including a floating piston. Alternatively, the dispenser may be connectable to a pressurized storage means including a sealed chamber defined by a storage means wall, an upper surface including the inlet valve and a lower surface including an externally threaded piston engageable with complementary internal threads in the storage means for pressurizing liquid disposed within the sealed chamber upon rotation of the piston.

The invention also provides a manually operable metered dispenser including a housing including a reciprocal frame member having a push-button connected thereto at a first end. The frame member and the push-button may be biased in a first direction. An inlet valve may be provided adjacent a second end for permitting entry of liquid product into a metering chamber defined by a cavity in the frame member. When the push-button is moved from an initial rest position toward a second generally opposite direction against the bias, a volume of the metering chamber is reduced to allow discharge of a metered dose of liquid product through a discharge orifice of a nozzle connected to the housing.

For the metered dispenser described above, the frame member may be integrally formed with the push-button. In a particular embodiment, the dispenser may be connectable to a pressurized storage container including a sealed chamber defined by a container wall. An upper surface may include the inlet valve and a lower surface may include a spring biased piston for pressurizing liquid disposed within the sealed chamber. The container may include a lower end having a removable container closure for retaining the spring biased piston. The container closure may include one or more release arms for retaining the spring biased piston in a first position. The release arm may further include a detent engageable by a piston plug insertable in an opening in the spring biased piston to release the spring biased piston from the first position for pressurizing liquid disposed within the sealed chamber. In a particular embodiment, the push-button may be spring biased in the first direction.

In alternative embodiments of the present invention, the aforementioned metered dispenser may be connectable to a storage container including a sealed chamber defined by a container wall, an upper surface including the inlet valve and a lower surface including a floating piston. Alternatively, the dispenser may be connectable to a pressurized storage container including a sealed chamber defined by a container wall, an upper surface including the inlet valve and a lower surface including an externally threaded piston engageable with complementary internal threads in the container for pressurizing liquid disposed within the sealed chamber upon rotation of the piston.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings:

FIG. 3 is an enlarged partial front sectional view of the metered dispenser of FIG. 1, illustrating the dispenser in the unloaded configuration;

FIG. 4 is a cross-sectional view of the metered dispenser of FIG. 1, taken substantially along line 4-4 in FIG. 3;

DETAILED DESCRIPTION OF THE EMBODIMENTS

Figure 7:
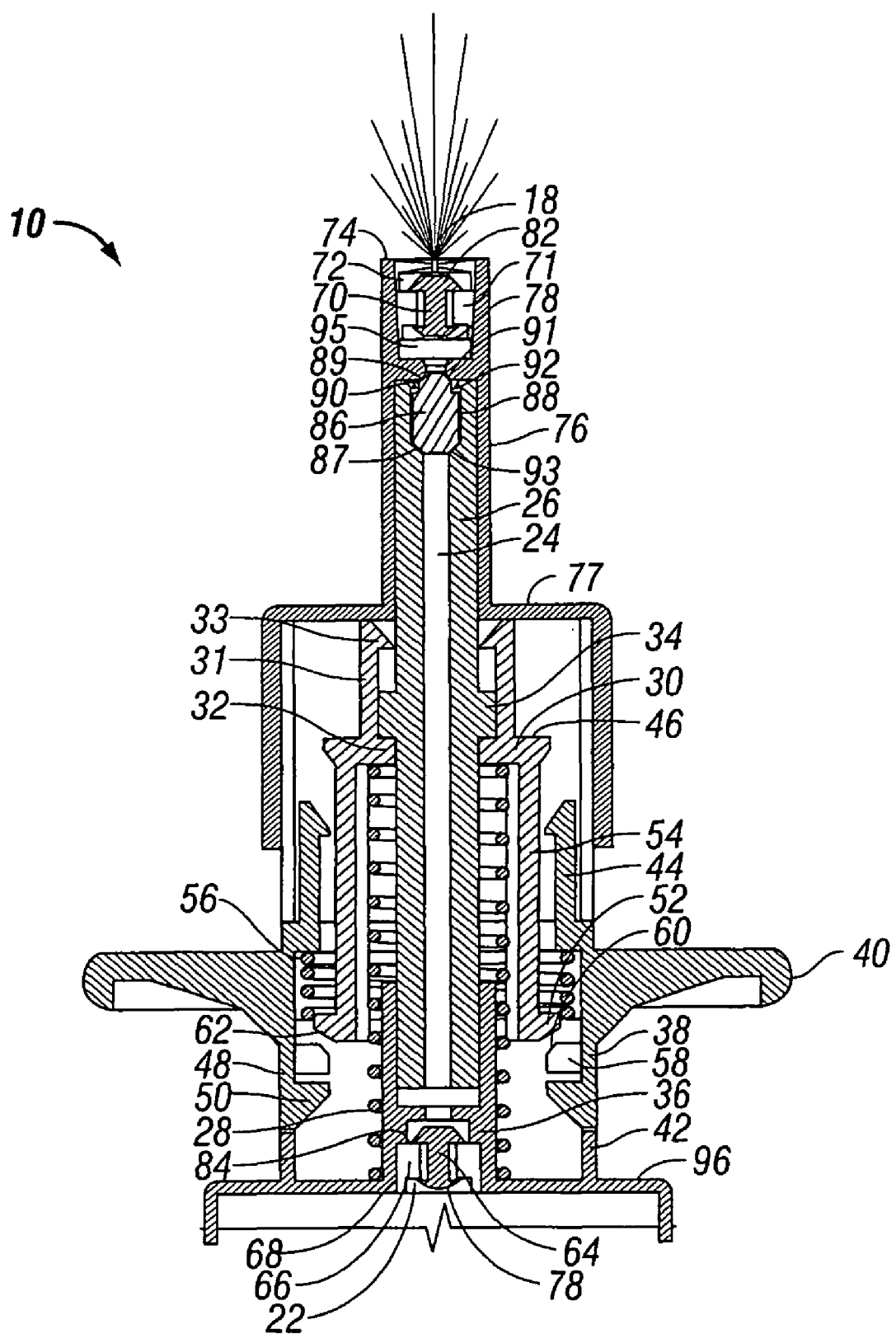
FIG. 7 is an enlarged partial front sectional view of the metered dispenser of FIG. 1, illustrating the dispenser in a discharge configuration after loading.
Figure 8:
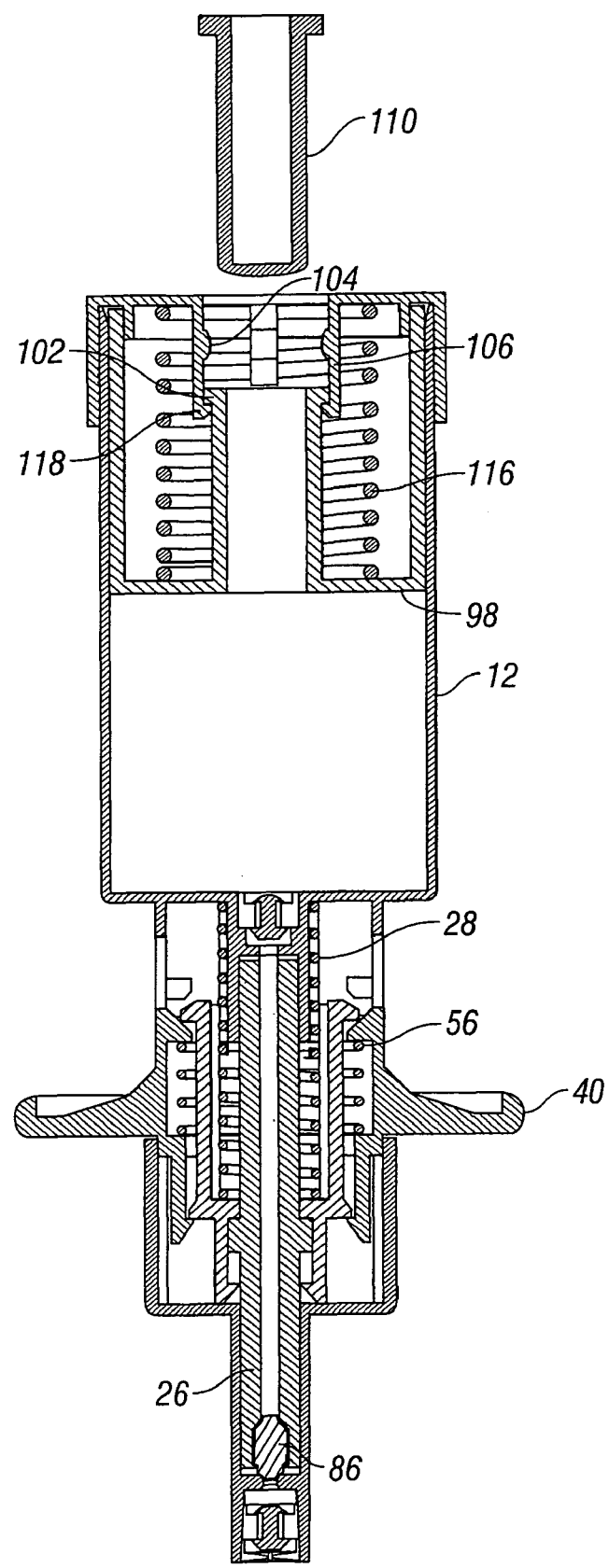
FIG. 8 is an enlarged front sectional view of the metered dispenser of FIG. 1, illustrating the dispenser in an inverted configuration for injection of liquid product within the container.
Figure 9:
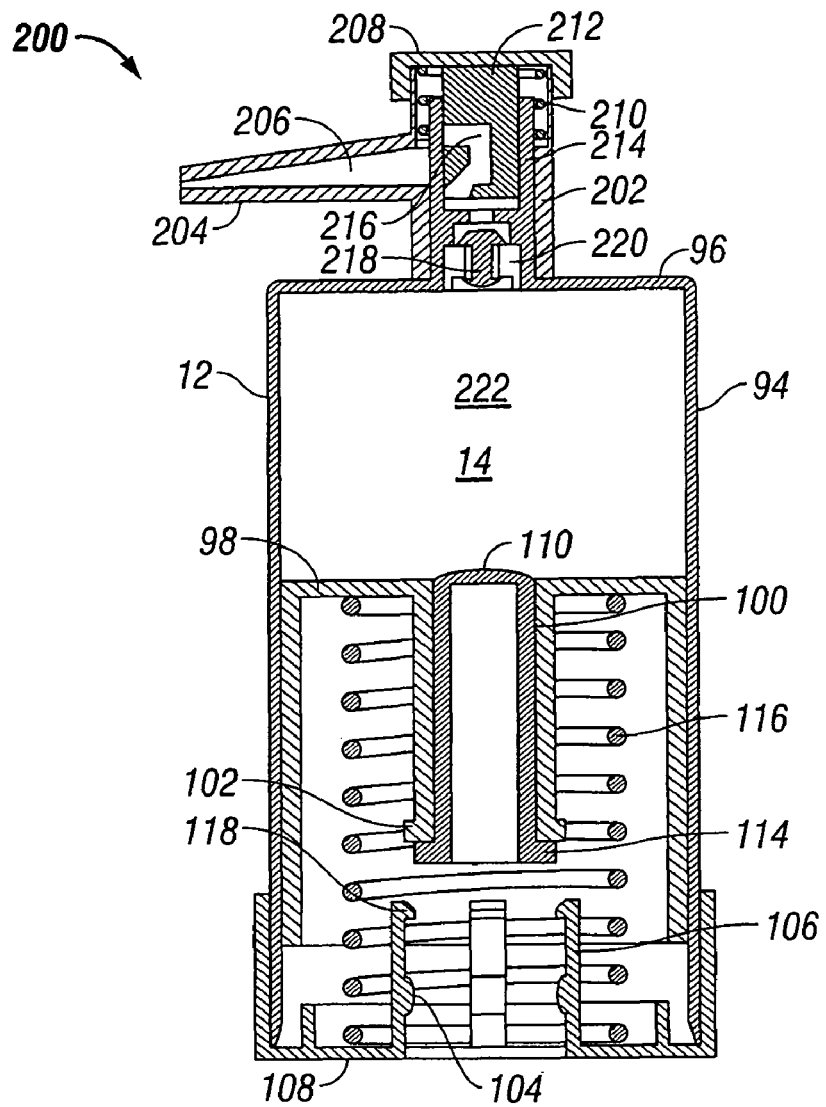
FIG. 9 is a front sectional view of another embodiment of a metered dispenser according to the present invention, illustrating the dispenser in an unloaded configuration.
Figure 10:
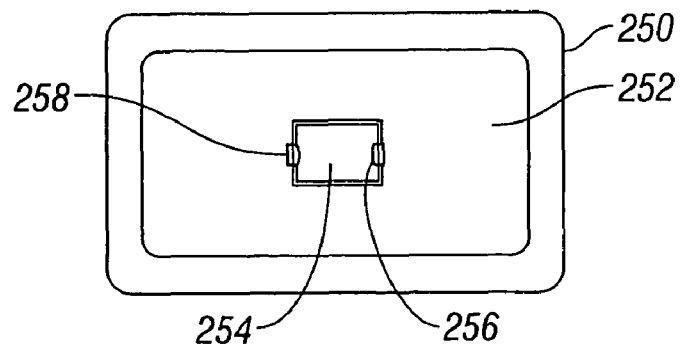
FIG. 10 is a bottom view of yet another embodiment of a metered dispenser according to the present invention, usable in conjunction with the embodiments of FIGS. 1 and 9.
Figure 11:
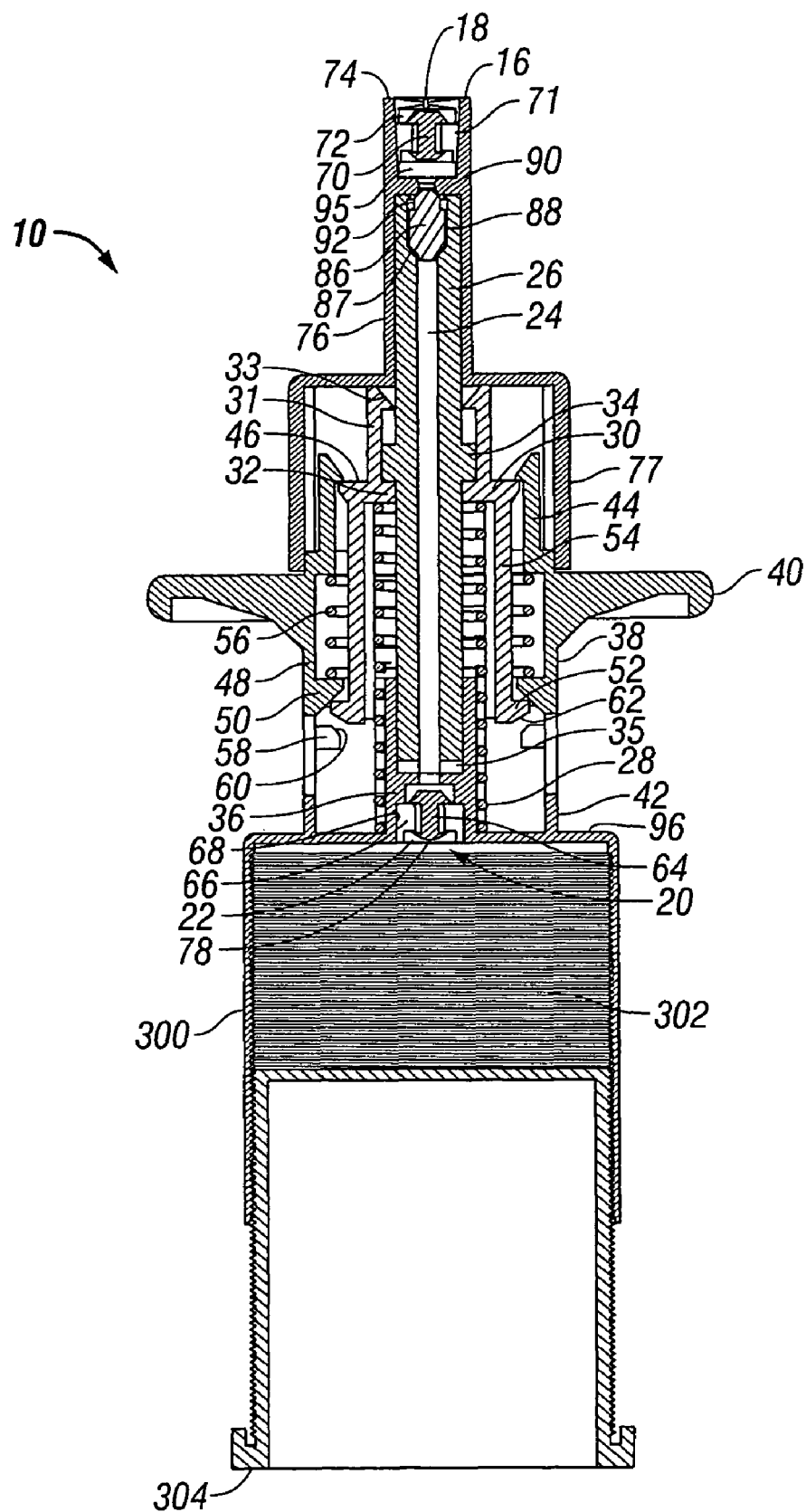
FIG. 11 is a front sectional view of another embodiment of a metered dispenser according to the present invention, illustrating the dispenser in an unloaded configuration.

Referring now to the drawings wherein like reference numerals designate corresponding parts throughout the several views, FIGS. 1-8 illustrate a mechanically propelled metered dispenser according to the present invention, generally designated "metered dispenser 10." FIGS. 9-11, respectively, illustrative further embodiments of the present invention.

Figure 1:
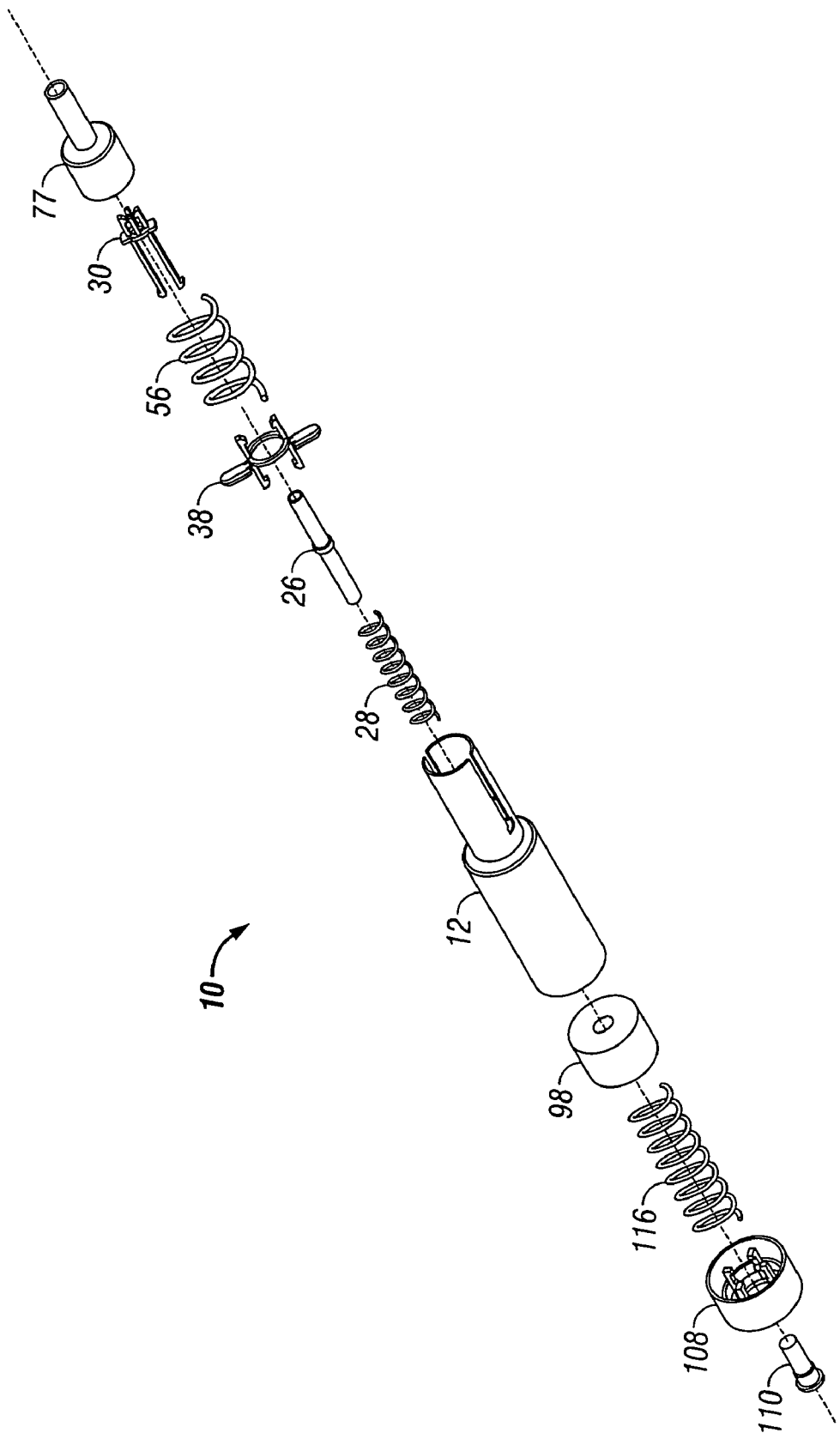
FIG. 1 is an exploded view of an embodiment of a metered dispenser according to the present invention, illustrating various components of the metered dispenser and an exploded view of an exemplary pressurized container for mounting the dispenser.
Figure 2A:
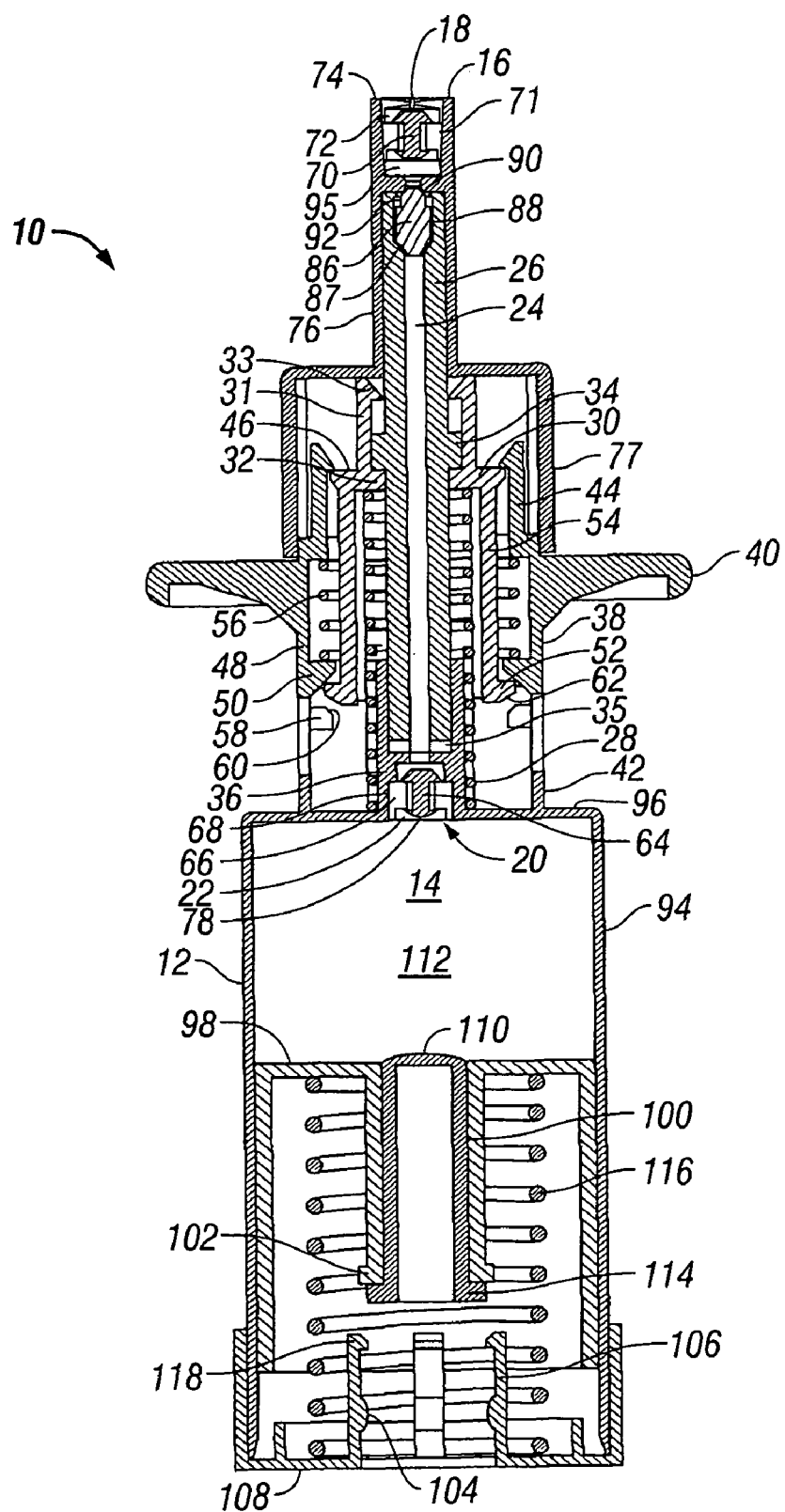
FIG. 2(a) is a front sectional view of the metered dispenser of FIG. 1, illustrating the dispenser in an unloaded configuration, and mounted to the exemplary pressurized container of FIG. 1.

Referring to FIGS. 1 and 2(a), metered dispenser 10 may be generally mounted on a pressurized storage container 12 of the type illustrated in FIGS. 1 and 2(a), or another similar pressurized container known in the art, for dispensing, for example, medicinal liquid 14 or other products which required dispensing of a metered dosage. As shown in FIGS. 2(a) and 3, metered dispenser 10 may generally include an upper end 16 having a discharge orifice 18 and a lower end 20 having an inlet port 22. Orifice 18 may be fluidly connected to inlet port 22 via passage 24 provided in piston drive stem 26, and may be configured to dispense liquid product 14 in the form of a liquid stream or a fine mist. Piston drive stem 26 may be biased upwardly by means of first internal spring 28, which engages a loading mechanism 30 to bias stem 26 upwards by means of the engagement of shoulders 32, 34 respectively provided on loading mechanism 30 and stem 26. Loading mechanism 30 may further include at least two rigid arms 31 including catch elements 33 engageable with shoulder 34 of piston drive stem 26. In the particular embodiment illustrated, four symmetrically disposed rigid arms 31 may be provided. Piston drive stem 26 may be guided at its lower end for vertical reciprocation within a stem guide 36 and define a receiving chamber 35 between the lower-most end of piston drive stem 26 and the adjacent surface of stem guide 36.

Figure 5:
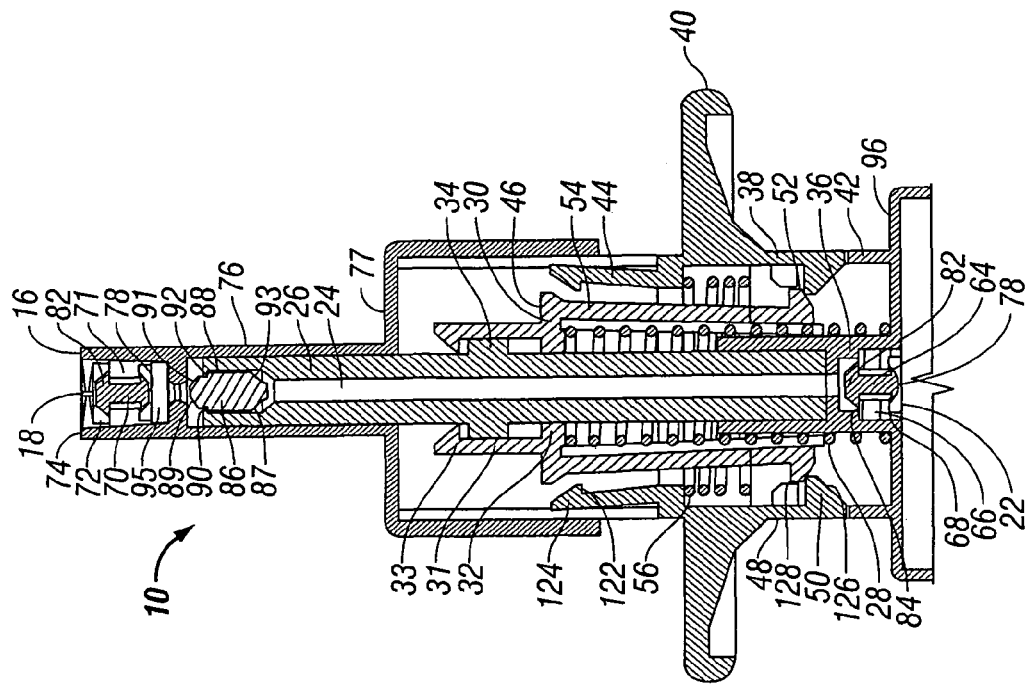
FIG. 5 is an enlarged partial front sectional view of the metered dispenser of FIG. 1, illustrating the dispenser in a loaded configuration.
Figure 6:
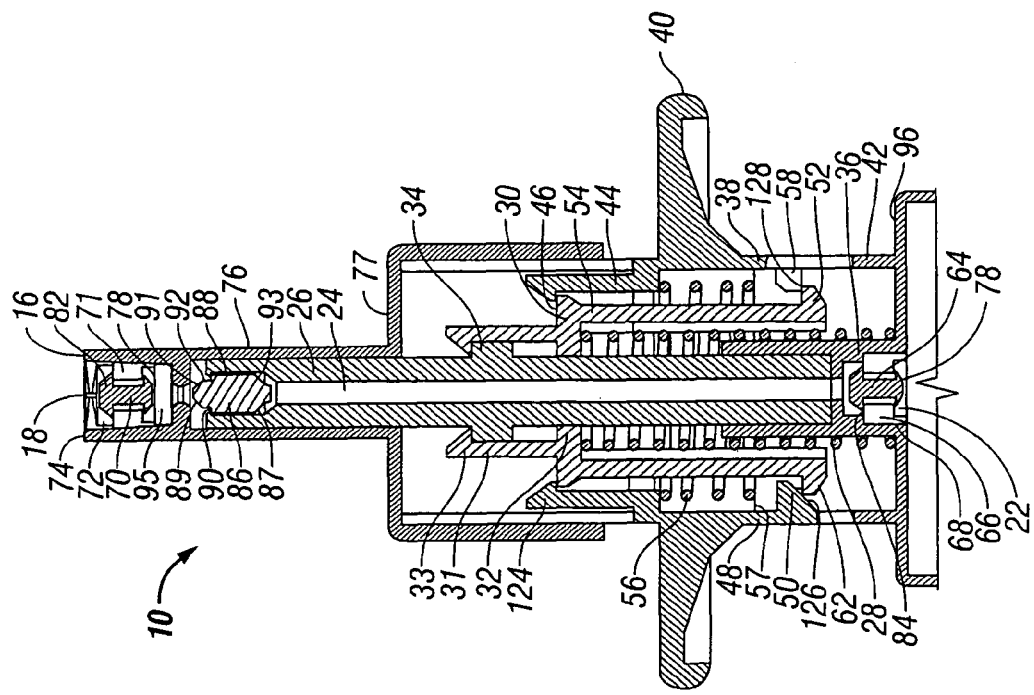
FIG. 6 is an enlarged partial front sectional view of the metered dispenser of FIG. 1, illustrating the dispenser just after being loaded and prior to being discharged.

A cocking mechanism 38 including a handle 40 may be provided for actuating metered dispenser 10. Cocking mechanism 38 may be disposed for reciprocation within dispenser housing 42 and include a plurality of flexible arms 44 engageable with upper surface 46 of loading mechanism 30. In the particular embodiment illustrated, two flexible arms 44 may be provided. Further, housing 42 may be formed with container 12 as shown, or may be otherwise formed separately and attached to container 12 by adhesive, threadeadly or other means known in the art. In this manner, a completely separate metered dispenser 10 may be manufactured, assembled and thereafter attached to a variety of pressurized containers. Cocking mechanism 38 may further include at least two legs 48 including release tabs 50 which are engageable with catch elements 52 provided on legs 54 of loading mechanism 30. In the particular embodiment illustrated, two legs 48 and 54 may be provided. A second internal spring 56 may bias cocking mechanism 38 upwards to the unloaded position illustrated in FIGS. 2(a) and 3. As shown in FIG. 5, spring 56 may engage a support 57 in housing 42 for retention thereof in the housing. As discussed below, at least two complementary stops 58 may be provided on dispenser housing 42 for engagement with catch elements 52. Stops 58 may each include a tapered edge 60 engageable with complementary tapered edge 62 of catch elements 52 for deflecting elements 52 radially inwards as shown in FIG. 6, and discussed in greater detail below.

Referring still to FIGS. 2(a) and 3, metered dispenser 10 may include a first one way inlet valve 64 held in place by an insert 66 disposed in lower portion 68 of stem guide 36. Further, a second one way inlet valve 70 may be disposed in an insert 71 or in an area 72 formed at upper end 74 of hollow stem 76. Stem 76 may include an integrally formed cap 77 which allows retention of the internal components of dispenser 10 on housing 42. As shown in FIGS. 2(a)-4, valves 64, 70 may each include a lower flexible portion 78 including a plurality of slits 80 for permitting flow of liquid 14 from container 12 into passage 24 when dispenser 10 is disposed in the unloaded configuration of FIG. 1. Further, valves 64, 70 may each include an upper rigid portion 82 which engages upper surface 84 of insert 66 or the upper surface of insert 71 to effectively prevent flow of liquid product from passage 24 back to container 12.

As shown in FIGS. 2(a) and 3, a floating valve piston 86 may be provided in upper cavity 88 of piston drive stem 26. Piston 86 may be retained within cavity 88 by means of a circular ring 90 on drive stem 26 engageable with detent 92 on piston 86.

Referring next to FIGS. 1 and 2(a), for the exemplary pressurized storage container 12 illustrated, container 12 may generally include an outer shell 94 having an upper surface 96 onto which housing 42 can be formed with shell 94 or otherwise threadeadly or adhesively mounted to enable attachment of dispenser 10. An inner piston 98 may be disposable within outer shell 94 and include a central opening 100 for permitting container 12 to be filled with liquid product 14. Central opening 100 may include a circular catch 102 at a bottom area thereof, with catch 102 being engageable with circular detent 104 provided on release arm 106 of container closure 108. A piston plug 110 may be sealingly insertable into central opening 100 for sealing chamber 112 within container 12. Piston plug 110 may include a circular catch 114 engageable with the bottom of catch 102, and be sized for a friction fit within opening 100. A spring 116 may be provided within inner piston 98 for biasing piston 98 upwards as illustrated in FIG. 1.

Referring to FIG. 8, container 12 is illustrated prior to being filled with liquid product 14. As illustrated, in order to fill container 12 with liquid product and pressurize the container by means of inner piston 98, piston 98 may first be disposed within outer shell 94, such that ring 118 on release arm 106 is engaged with circular catch 102 to hold piston 98 in the position shown. With spring 116 disposed as shown within piston 98, container closure 108 may be slid onto outer shell 94 to retain inner piston 98 and spring 116 within shell 94. With container 12 inverted, liquid product 14 may then be injected into container 12 through central opening 100. With container 12 still in an inverted configuration, piston plug 110 may be inserted into central opening 100 to seal chamber 112. Alternatively, instead of injecting liquid into container 12 through central opening 100, the liquid may be placed in container 12 in the inverted configuration illustrated, and container closure 108 having piston 98 attached as a unit may be slid onto the outer shell 94 of container 12 to achieve the same results. This would of course provide a larger area for injection of liquid into container 12. As piston plug 110 is inserted, circular catch 114 on the bottom of piston plug 110 may contact circular detent 104 to deflect release arm 106 outwardly and thus release inner piston 98 within shell 94. In this manner, as the volume of liquid product 14 within chamber 112 is reduced, inner piston 98, which has piston plug 110 sealingly inserted therein, is biased upwards by means of spring 116 to pressurize chamber 112.

Figure 2B:
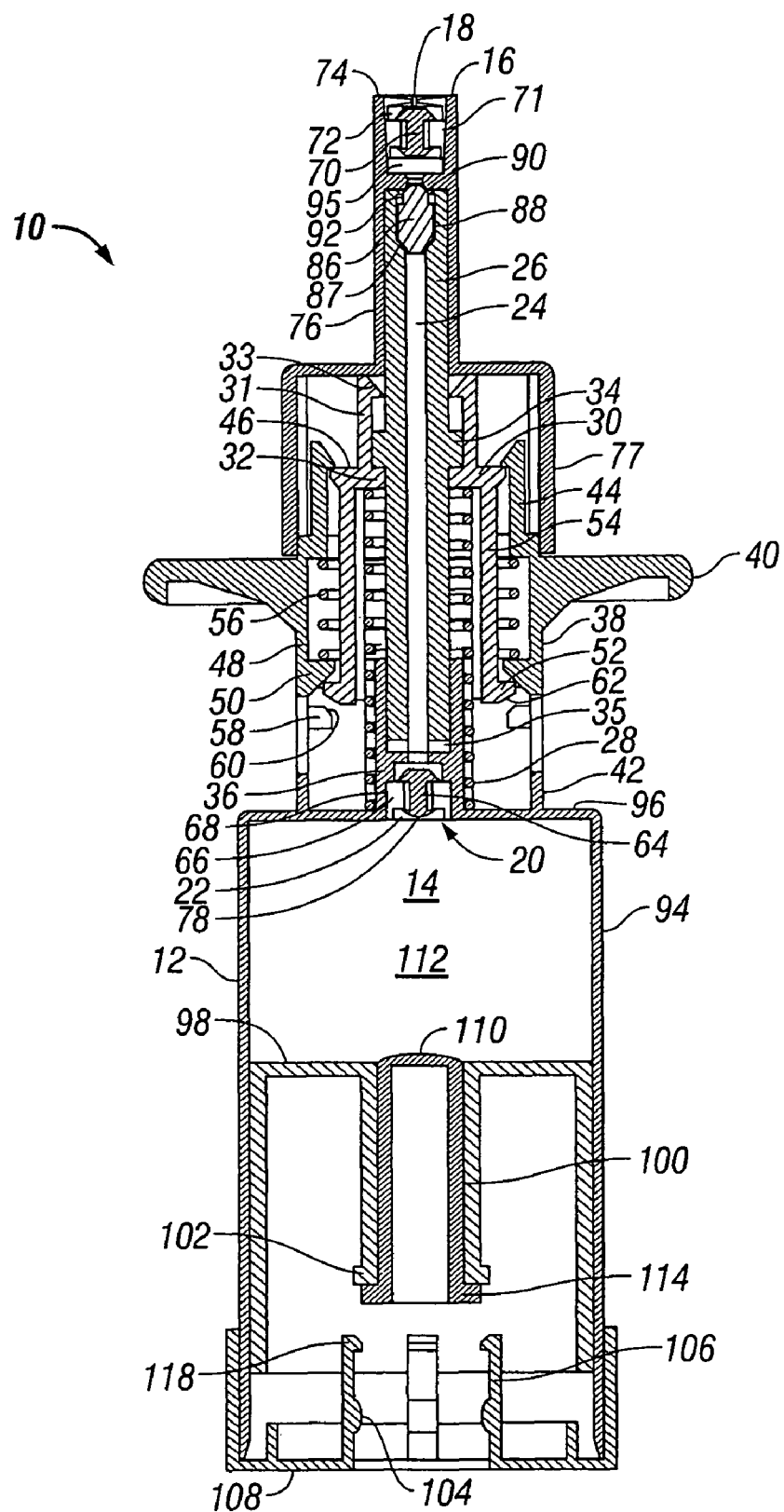
FIG. 2(b) is a front sectional view of the metered dispenser of FIG. 1, illustrating the dispenser in an unloaded configuration, and mounted to the exemplary container with a floating piston of FIG. 1.

According to an alternative embodiment shown in FIG. 2(b), dispenser 10 may be attached to a container with a floating piston. In this embodiment, piston drive stem 26, when moving in the direction of bias of spring 28, may suck liquid product 14 from container 12 through inlet port 22 into passage 24. The amount of liquid suctioned may be determined by the size of receiving chamber 35 as well as the stroke parameters of piston drive stem 26.

Referring next to FIGS. 3 and 5-7, metered dispenser 10 is respectively illustrated in unloaded, loaded, prior to discharge and discharge configurations. The operation of metered dispenser 10 will therefore be described in detail with reference to FIGS. 2(a)-7.

Specifically, as illustrated in FIGS. 2(a) and 3, metered dispenser 10 is illustrated in an unloaded configuration, with springs 28 and 56 disposed in their fully extended positions. In the unloaded configuration of FIGS. 2(a) and 3, inner piston 98 having piston plug 110 sealingly disposed therein may pressurize chamber 112 to force liquid product into passage 24 via first one way inlet valve 64. Additionally, valve seat 87 of piston drive stem 26 may push floating valve piston 86 upwards so that upper area 89 of piston 86 contacts upper valve seat 91 to effectively close passage 24. In order to discharge product 14 out through discharge orifice 18, a user may grasp container 12 having metered dispenser 10 mounted thereon in the palm of their hand and with the fore and middle fingers contacting handle 40, the user may pull handle 40 downwards.

As handle 40 is being pulled downwards to the loaded position of FIG. 5, flexible arms 44 of cocking mechanism 38 pull loading mechanism 30 downwards until catch elements 33 on arms 31 contact the upper surface of shoulder 34. At this position, catch elements 33 prevent loading mechanism 30 from being moved further downwards. Further, from the transition of handle 40 from the FIG. 3 to the FIG. 5 position, tapered edges 62 of catch elements 52 contact tapered edges 60 of stops 58 to deflect legs 54 radially inwards until catch elements 52 snap under stops 58 as shown in FIG. 5. Additionally, the contact between piston 86 and valve seat 87 is released to allow piston 86 to "float" within area 93, and thus simultaneously allow liquid product 14 present in passage 24 to enter into metering chamber 95.

Referring to FIGS. 5 and 6, as handle 40 is pulled further downwards, the frictional contact between edges 122 of fingers 124 of flexible arms 44 is overcome to allow arms 44 to spread apart and thus allow further downward movement of cocking mechanism 38. During the further downward movement of cocking mechanism 38, tapered edges 126 of release tabs 50 on legs 48 contact edge 128 of catch elements 52 to deflect legs 54 radially inwards to release catch elements 52 from under stops 58 as shown in FIG. 6.

Referring to FIGS. 6 and 7, upon release of catch elements 52 from under stops 58, piston drive stem 26 is projected upwards with piston 86 under the bias of spring 28, such that valve seat 87 which is disposed in contact with piston 86 projects piston 86 upwards and thus reduces the volume of metering chamber 95 to discharge liquid product through discharge orifice 18 as shown. In this manner, a precisely metered amount of liquid product present in metering chamber 95 is discharged through discharge orifice 18. Once the upper area 89 of piston 86 contacts valve seat 91 and the lower area 93 of piston 86 contacts valve seat 87, further flow of liquid product into metered chamber 95 is shut off. In a particular embodiment of the present invention, metering chamber 95 may be sized to discharge approximately 50-140 micro-liter of product through discharge orifice 18 for nasal usage, and may be otherwise sized to discharge approximately 15-25 micro-liter of product for eye-care usage.

Referring to FIGS. 2(a), 3 and 7, in order to reset metered dispenser 10 for further actuation, handle 40 may be released to the position of FIG. 2(a), whereby a user may simply pull handle 40 as discussed above with reference to FIGS. 2(a), 3 and 5-7 to actuate and dispense additional metered doses of liquid product through discharge orifice 18.

Referring next to FIG. 9, another embodiment of the invention will now be described in detail, with this embodiment being generally referred to as "metered dispenser 200."

Specifically, as shown in FIG. 9, metered dispenser 200 may generally include the dispenser being mounted on a pressurized storage container, and in the particular embodiment illustrated, dispenser 200 may be mounted on a container 12 similar to the container illustrated in FIG. 2(a). Metered dispenser 200 may generally include a housing 202 including a horizontally extending nozzle 204 having a tapered discharge passage 206. A spring biased push-button 208 may be reciprocally mounted on housing 202, with a spring 210 disposed within the housing as shown for biasing push-button 208. Push-button 208 may be mounted on a reciprocal frame 212, which together with internal frame 214, defines a metering chamber 216. In the particular embodiment illustrated, internal frame 214 may be formed with container 12, but as with metered dispenser 10, the components of dispenser 200 may be formed separately, assembled as a unit, and thereafter attached to a variety of pressurized containers. A one-way inlet valve 218, similar to valve 64 for metered dispenser 10 may be mounted by insert 220 to permit pressurized liquid product 14 to enter into chamber 216.

In operation, in order to dispense liquid product through the outlet orifice of nozzle 204, a user may grasp container 12 having dispenser 200 mounted thereon. By using a thumb, the user may press push-button 208 downwards so that pressurized product present in metering chamber 216 is expelled out through the outlet orifice of nozzle 204. During pressing of push-button 208, one-way inlet valve 218 may seal metering chamber 216 to prevent return of liquid product present in chamber 216 into container 12. Further, upon release of push-button 208, spring 210 may bias push-button 208 upwards, and during this movement of push-button 208, additional liquid product may enter into metering chamber 216 by means of the pressure created by inner piston 98, as discussed above.

Referring next to FIGS. 2(a) and 10, another pressurized storage container 250 will now be described in detail.

Specifically, as shown in FIG. 10, compared to container 12, container 250 may include a generally rectangular profile. In this regard, container 250 may include a rectangular inner piston 252 into which a rectangular piston plug 254 is disposed and allows for the release of piston 252 by means of engagement with circular detent 256 provided on release arm 258, in a similar manner as circular detent 104 provided on release arm 106 for the embodiment of FIG. 2(a). As apparent to those skilled in the art, a metered dispenser 10 or 200 may be mounted to container 250 in a similar manner as discussed above for container 12.

Referring next to FIGS. 2(a) and 11, another pressurized storage container 300 will now be described in detail.

Specifically, as shown in FIG. 11, compared to container 12, container 300 may be internally threaded at 302 for complementary engagement with an externally threaded piston 304. In order to pressurize the liquid within container 300, piston 304 may be rotated as needed for movement towards the dispenser, and for thereby dispensing of the pressurized liquid in the manner discussed above.

To summarize, the present invention thus provides a metered dispenser which is repeatable in operation to dispense a predetermined dosage of medicine or other product, and is usable by a broad range of users to repeatedly dispense a metered dosage of medicine without fluctuations in the amount of medicine dispensed, or without the dispenser being readily susceptible to contamination during use.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

INDEX OF REFERENCE NUMBERS

10 . . . metered dispenser
12 . . . pressurized storage container
14 . . . liquid
16 . . . upper end
18 . . . discharge orifice
20 . . . lower end
22 . . . inlet port
24 . . . passage
26 . . . piston drive stem
28 . . . first internal spring
30 . . . loading mechanism
31 . . . rigid arm
32 . . . shoulder
33 . . . catch element
34 . . . shoulder
35 . . . receiving chamber
36 . . . stem guide
38 . . . cocking mechanism
40 . . . handle
42 . . . dispenser housing
44 . . . flexible arms
46 . . . upper surface
48 . . . legs
50 . . . release tabs
52 . . . catch elements
54 . . . legs
56 . . . second internal spring
57 . . . support
58 . . . complementary stops
60 . . . tapered edge
62 . . . tapered edge
64 . . . first one way inlet valve
66 . . . insert
68 . . . lower portion
70 . . . second one way inlet valve
72 . . . area
74 . . . upper end
76 . . . hollow stem
77 . . . cap
78 . . . lower flexible portion
80 . . . slits
82 . . . upper rigid portion
84 . . . upper surface
86 . . . floating valve piston
87 . . . valve seat
88 . . . upper cavity
89 . . . upper area
90 . . . circular ring
91 . . . valve seat
92 . . . detent
93 . . . area
94 . . . outer shell
95 . . . metering chamber
96 . . . upper surface
98 . . . inner piston
100 . . . central opening
102 . . . circular catch
104 . . . circular detent
106 . . . release arm
108 . . . container closure
110 . . . piston plug
112 . . . sealing chamber
114 . . . circular catch
116 . . . spring
118 . . . ring
122 . . . edges
124 . . . fingers
126 . . . tapered edges
128 . . . edge
200 . . . metered dispenser
202 . . . housing
204 . . . horizontally extending nozzle
206 . . . tapered discharge passage
208 . . . push-button
210 . . . spring
212 . . . reciprocal frame
214 . . . internal frame
216 . . . metering chamber
218 . . . one-way inlet valve
220 . . . insert
250 . . . pressurized storage container
252 . . . rectangular inner piston
254 . . . rectangular piston plug
256 . . . circular detent
258 . . . release arm

What is claimed is:

1. A manually operable metered dispenser comprising:
a housing including a reciprocal piston drive stem including an inlet opening at a first end thereof, a floating piston disposed at a second end thereof, and a passage between said first and second ends;
an inlet valve provided adjacent said first end for permitting entry of liquid product into said passage, and an outlet valve provided adjacent said second end;
a cocking mechanism reciprocally disposed substantially within said housing, and biased in a first direction; and
a loading mechanism biased in said first direction, movable in a second generally opposite direction by said cocking mechanism, and engageable with said piston drive stem to move said piston drive stem in said second direction, said loading mechanism being further engageable with at least one stop provided in said housing,
wherein when said cocking mechanism is moved from an initial rest position toward said second direction, said cocking mechanism moves said loading mechanism and along therewith said piston drive stem in said second direction, further, during movement of said loading mechanism in said second direction, said loading mechanism engages said stop, and during continued movement of said cocking mechanism in said second direction, said loading mechanism is disengaged from said stop to project in said first direction by said loading mechanism bias, and along therewith, project said piston drive stem in said first direction to dispense a metered dose of liquid product through a discharge orifice provided adjacent said second end; and,
wherein said dispenser is connectable to a storage container including a sealed chamber defined by a container wall, wherein said container includes a rectangular profile.

2. A manually operable metered dispenser according to claim 1, wherein said cocking mechanism includes a handle for permitting manual movement of said cocking mechanism toward said second direction.

3. A manually operable metered dispenser according to claim 1, wherein said inlet and outlet valves are one-way valves for respectively permitting flow of pressurized liquid product into said passage and out through said discharge orifice.

4. A manually operable metered dispenser according to claim 1, wherein said cocking mechanism is biased by a first coil spring disposed substantially around said loading mechanism, and said loading mechanism is biased by a second coil spring disposed substantially around said piston drive stem, said first coil spring has a diameter greater than said second coil spring.

5. A manually operable metered dispenser according to claim 1, wherein said loading mechanism includes at least one substantially rigid arm including a catch element engageable with a shoulder on said piston drive stem for moving said piston drive stem in said second direction.

6. A manually operable metered dispenser according to claim 1, wherein said loading mechanism includes at least one leg including a catch element engageable with said stop to retain said loading mechanism in a loaded configuration during said movement of said cocking mechanism from said initial rest position toward said second direction.

7. A manually operable metered dispenser according to claim 1, wherein said loading mechanism catch element includes a tapered surface engageable with a respective tapered surface on said stop to deflect said loading mechanism leg radially inwards and allow engagement of said loading mechanism catch element with said stop during said movement of said cocking mechanism from said initial rest position toward said second direction.

8. A manually operable metered dispenser according to claim 1, wherein said cocking mechanism includes at least one leg including a release tab engageable with said catch element on said loading mechanism leg to disengage said loading mechanism from said stop during said continued movement of said cocking mechanism in said second direction.

9. A manually operable metered dispenser according to claim 1, wherein said release tab includes a tapered surface for moving said catch element on said loading mechanism leg radially inwards to disengage said loading mechanism from said stop.

10. A manually operable metered dispenser according to claim 1, wherein said cocking mechanism includes at least one flexible arm including a finger engageable with said loading mechanism, said flexible arm being deflected outwards during said continued movement of said cocking mechanism in said second direction to release said loading mechanism from said cocking mechanism and allow said loading mechanism to project said piston drive stem toward said first direction.

11. A manually operable metered dispenser according to claim 1, wherein said dispenser is connectable to a pressurized storage container including a sealed chamber defined by a container wall, an upper surface including said inlet valve and a lower surface including a spring biased piston for pressurizing liquid disposed within said chamber.

12. A manually operable metered dispenser according to claim 1, wherein said container includes a lower end having a removable container closure for retaining said spring biased piston, said container closure includes at least one release arm for retaining said spring biased piston in a first position, said release arm further includes a detent engageable by a piston plug insertable in an opening in said spring biased piston to release said spring biased piston from said first position for pressurizing liquid disposed within said chamber.

13. A manually operable metered dispenser according to claim 1, wherein said dispenser is connectable to a storage container including a sealed chamber defined by a container wall, an upper surface including said inlet valve and a lower surface including a floating piston.

14. A manually operable metered dispenser according to claim 1, wherein when said cocking mechanism is moved from said initial rest position toward said second direction, said floating piston is allowed to move within an area at said second end to allow liquid product to enter from said passage into a metering chamber between said floating piston and said outlet valve for allowing said metered dose of liquid product to be dispensed through said discharge orifice when said piston drive stem is projected in said first direction.

15. A manually operable metered dispenser according to claim 1, wherein said cocking mechanism is spring biased to return to said initial rest position.

16. A manually operable metered dispenser according to claim 1, wherein said dispenser is usable for at least one of nasal and eye-care.

17. A manually operable metered dispenser according to claim 1, wherein said metered dose being dispensed as a spray or a fine mist.

* * * * *